United States Patent
Harms et al.

(10) Patent No.: US 6,968,284 B2
(45) Date of Patent: Nov. 22, 2005

(54) METHOD FOR THE ANALYSIS AND EVALUATION OF MEASURED VALUES OF AN OPEN TEST SYSTEM

(75) Inventors: Klaus-Christoph Harms, Graz (AT); Christian Beidl, Eggersdorf (AT)

(73) Assignee: AVL List GmbH, Graz (AT)

( * ) Notice: Subject to any disclaimer, the term of this patent is extended or adjusted under 35 U.S.C. 154(b) by 41 days.

(21) Appl. No.: 10/107,802

(22) Filed: Mar. 28, 2002

(65) Prior Publication Data

US 2002/0139166 A1 Oct. 3, 2002

(30) Foreign Application Priority Data

Mar. 28, 2001 (AT) ............................. GM227/2001

(51) Int. Cl.$^7$ ........................... G06F 19/00; G06F 9/00
(52) U.S. Cl. .................... 702/108; 702/179; 702/182; 702/183; 714/733; 714/800
(58) Field of Search ....................... 702/108, 116, 123, 702/179, 182–185; 324/73.1, 415; 700/29; 701/34; 705/8; 370/245; 714/800

(56) References Cited

U.S. PATENT DOCUMENTS

| | | | | |
|---|---|---|---|---|
| 5,062,055 A | * | 10/1991 | Chinnaswamy et al. | .... 702/182 |
| 5,130,936 A | * | 7/1992 | Sheppard et al. | ........... 702/123 |
| 5,557,620 A | * | 9/1996 | Miller, Jr. et al. | .......... 714/733 |
| 5,661,735 A | * | 8/1997 | Fischer | ....................... 371/49.1 |
| 5,835,886 A | * | 11/1998 | Scheil | ......................... 702/179 |
| 6,208,963 B1 | * | 3/2001 | Martinez et al. | ............ 704/232 |
| 6,343,261 B1 | * | 1/2002 | Iwanowski et al. | ......... 702/183 |
| 6,385,201 B1 | * | 5/2002 | Iwata | ......................... 370/400 |

* cited by examiner

*Primary Examiner*—Michael Nghiem
*Assistant Examiner*—John Le
(74) *Attorney, Agent, or Firm*—Dykema Gossett PLLC

(57) ABSTRACT

In a method for the analysis and evaluation of measured values of an open test system, a test piece is monitored during a test run by at least one signal channel which sends a signal to an evaluation unit for further processing whereby at least one plausibility node is coupled with at least one signal channel. In order to allow a statement to be made about the value of plausibility nodes and their results in relation to a specific measuring task, an evaluated plausibility is ascertained for at least one of the measured values from the type and number of plausibility nodes as well as their possible, variable interconnection.

In order to permit, in addition, statements on the reliability of the results of the test system in relation to the desired measured values, it is provided that from the type and number of available plausibility nodes in combination with the type and number of available signal channels, a value is ascertained for the confidence level of the plausibility of at least one of the measured values of the current test system.

9 Claims, No Drawings

METHOD FOR THE ANALYSIS AND EVALUATION OF MEASURED VALUES OF AN OPEN TEST SYSTEM

BACKGROUND OF THE INVENTION

1. Field of the Invention

The invention relates to a method for analyzing and evaluating measured values of an open test system where, during a test run, a test piece is monitored by at least one signal channel which sends a signal to an evaluation unit for further processing whereby at least one plausibility node is coupled with at least one signal channel.

2. The Prior Art

Testing and measuring systems for research and development, in particular in motor vehicle technology and for the engine and drive train of a vehicle, for example, have today, by necessity, become themselves almost unmanageably complex and highly sophisticated products. In relatively short test periods, enormous quantities of test data occur and are recorded or stored. User-friendly software tools make even extensive evaluations of measured data possible, which are used for evaluating test runs and the test piece, and in particular for the optimization of its desired performance criteria. Furthermore, there are new types of software packages for the automatic carrying out of test runs and for the automatic determination of optimum operating points of the test piece, which significantly contribute to the reduction in development time and to an improvement of the quality of development results and the products themselves.

For such test runs, test stands (but also mobile measuring equipment or devices) are often in operation for hours and the development result depends on whether the entire system has worked without errors through-out this long test period. The user has to be able to rely on the fact that the measured and test data are significant and usable. A critical error, e.g. a changed sensitivity of a sensor, can cause not only enormous costs (test stand costs, equipment and consumables costs, test piece costs, personnel costs, etc.), but can also, most of all, have the effect of a delay in the development process, which is associated with extreme costs and competitive disadvantages. For example, software products for the automation of test runs and for the automatic optimisation of, say, engine operating conditions are, to a high degree, dependent on the reliability of the test run data. A setup that guarantees the plausibility of test results and detects non-permissible deviations early, significantly enhances the utility and economy of this software product.

Of course, methods for detecting error conditions are already known as, for example, from DE 198 41 260 A1 for error conditions in motor vehicles. With the aid of local diagnosis modules for partial systems of the vehicle, the function of said partial system is monitored and used for its control or for other partial systems. But measured values of the various partial systems are not checked at all, nor is their plausibility.

It is therefore necessary that the above-mentioned testing and measuring systems are equipped with a setup which, to the highest possible degree, can guarantee the usability of test results. The plausibility and quality of the measured results obtained have to be checked automatically and indicated to the user—not only after a test run has been carried out, i.e. when data is evaluated based on the recorded measured data, but as early as possible, preferably during the test run itself. An example of such a plausibility check, which in general can also be called a FDIC (Failure Detection, Isolation and Correction) method, is described in the EP 0 720 004 B1.

At present, such plausibility and measured data quality checking devices are only available in a very modest range and usually only relate to strictly defined and self-contained measuring instruments and measuring systems. It is known that some measuring instruments carry out a self test at the start of a test run and that, during the test run, certain function tests can be carried out on the measuring instruments. Some measuring systems also have calibration and diagnosis options that can be called up as required. There are also individually parametrisable monitoring options for, for example, critical values and the smoothness of individual measured signals. Thus, for example, a method is described in WO96/13764 where for an individual measured value a comparison is carried out with specific parameters of the measuring system itself as well as a second comparison with rules characteristic for the monitored system, and where the result of this check is weighted.

It is noteworthy, though, that for complex measuring tasks, e.g. on test stands in the vehicle industry, in particular on motor test benches, there are many measuring chains in existence. Depending on the test run aim, i.e. the conclusions to be drawn for the test piece from the test run, these individual measuring chains have differing relevance. The plausibility of an individual measured value, which has been ascertained by a FDIC method, for example, like the one described in the EP 0 720 004 B1, can have very different effects on the test run aim overall, which so far has not been taken into account in the commonly used methods. Particularly when performing test runs in the development and testing of complex equipment such as internal combustion engines, a clear evaluation of the reliability of measuring results is required in the interest of quality assurance, which goes beyond the plausibility of individual measured values. So far, the overall plausibility of a test run was generally examined by an experienced engineer who, on the one hand, could apply criteria from personal experience, but most of all consider correlations between measured data, based on techno-physical facts. Automated plausibility test systems capable of being adapted flexibly to the requirements of differing and complex testing and measuring systems, have not been created so far.

It is the object of the present invention, therefore, to provide a method by which a conclusion could be drawn about the value of plausibility nodes and their output in respect of a special measuring task. Thus, it is intended to provide a new generic approach based on a concept of general validity for evaluating measured data, in particular the evaluation of plausibility and quality of the measured and test data, an approach which allows the method to be carried out in consideration of the required, extensive test rules which in part are implemented in existing instruments and components of a measuring system, e.g. a test bench or also a mobile measuring instrument, and/or are provided in a software library. Furthermore, an additional object is a method with which it is possible to draw conclusions about the reliability of the test system results in relation to the desired measured values. As a further object, these methods should make the plausibility test system adaptable to the respective special task, i.e. the respective special test bench, the special measuring apparatus or similar and their actual configuration or, in terms of 'plug & measure', also largely be automatically adaptable.

DESCRIPTION OF THE INVENTION

For the solution of the first object, the method described above is characterised in that for at least one of the measured values an evaluated plausibility is ascertained from the type and number of plausibility nodes as well as their possible, variable interconnections between each other. Due to this variability in the linkages between plausibility nodes, the requirement of flexibility can already be satisfied: For, as a consequence of the great variety of test tasks, test piece and test system as well as the test runs carried out can represent unique situations to a certain extent. In contrast to the known "weighting" of the measured value (to be seen as value or "content") of a measured quantity for ascertaining a plausibility value for a measured value (again to be seen as value or content), the evaluation of the plausibility conclusion belonging to a measured quantity (to be seen as quantity or "structure") is itself carried out according to the present invention, independently of the associated measured value and its plausibility value, so that a plausibility is ascertained which is evaluated "dependently of the measuring structure" but, of course, "related to the measured value". Preferably, this is achieved with an object-oriented software architecture for typically a network of plausibility test nodes each of which can be adapted to the special application by loading from the library the plausibility test rules belonging to the current configuration of the measuring system, namely the currently relevant ones. Here, each rule is allocated to a respective node so that it suitably combines the required input data (measured values, symptomatic data of the simulation calculations carried out in parallel to the measurements, the parameters belonging to the test rule, etc.) and thus initially draws an individual plausibility conclusion in a known manner which is then passed on to a higher level evaluation and display module where the individual plausibility nodes are logically combined and their plausibility conclusions are then evaluated based on these logical relationships and possibly by considering the measuring aim. For, dependent on which aim is set for a test run, some measured values are to be regarded as critical or non-critical and, dependent on how much redundancy is contained in the test rules to be applied, a different weighting can be attributed to the plausibility statement.

In their most general form, the plausibility nodes are rules that produce a conclusion about the plausibility of the measured value delivered by this signal channel. The plausibility test rules to be used will mainly be based on techno-physical models. But test rules derived from the area of computer aided intelligence are also being considered. To a certain extent, the rules can be generally useful, quasi for any signal, for example for test rules, based on the analysis of individual signals, for the detection of locally erratic deviations in the signal shape. To a larger extent, though, the test rules will be based on the conditions of an actual type of test piece and test system and thus can frequently be associated with a specific group of measuring systems at hand. An example of that are the balance equations such as those in engine test runs for the mass flow of the air and fuel drawn in compared to the substances in the exhaust gas. Furthermore, complex test rules can also be used where the conformance of the real world with the virtual world of simulation calculations is to be found, for example for the plausibility evaluation of indicated combustion data from the analysis of the indicated high pressure and gas exchange phase of the combustion process.

The plausibility nodes can either be defined by the type and integration of the signal channel itself, by its internal circuitry architecture or similar, i.e. in hardware terms generally speaking, but can also be realised via software as well as by combinations of these two contrary types of systems.

In order to be able to achieve a quick plausibility evaluation which is easily adaptable to many different situations, at least some of the plausibility nodes are selected, according to a further characteristic of the invention, from a totality of plausibility nodes predefined in a library. In the library, starting with just a few up to the totality of the plausibility nodes can be stored. While the current configuration of a test run and thus the totality of the currently activated plausibility nodes must be contained in the library as a subset, it is still quite variable. This subset need not necessarily be determined by the operator alone and passed on to the system, but it can also have been worked out by artificial intelligence or can be optimised. It determines from the physical conditions (in relation to currently available measured quantities) and the software specific conditions (in relation to currently available, a priori known system parameters and virtual quantities of the simulation) just that current configuration and the test nodes to be activated.

The method in terms of the invention can be used both on-line for testing measured data already during the test run and off-line, e.g. for testing large data volumes subsequent to tests, e.g. in prototype vehicles on proving grounds.

According to a further characteristic it is provided that the library of plausibility nodes is extendable and changeable, e.g. with the aid of artificial intelligence. This means that new or extended plausibility nodes can be entered into the library of testing options, be it via programming by humans, by artificial intelligence, e.g. by a "learning capability", training of neuronal nets, etc. Thus, too, the required flexibility as already mentioned above, can be guaranteed to a still further extent.

According to a further characteristic of the invention, with modularity in mind, it is provided that the evaluated plausibility for the various partial systems is determined separately. For a test system practically always consists of several partial systems which, for example, represent intelligent sensors, measuring instruments and measuring systems with combined groups of signal channels. But this also takes into account the cascadability and extendability/upgradability: For any test bench is subject to changes regarding its equipment level in terms of measuring technology, and a plausibility test system should be capable to grow correspondingly, in this case especially by the combination of partial systems which can also be operated and monitored independently of each other.

In a method according to at least one of the previous paragraphs, advantageously according to a further characteristic of the invention, a value for the confidence level of the plausibility of at least one of the measured values of the current test system can be determined from the type and number of the available plausibility nodes in combination with the type and number of the available signal channels. Just by the configuration of the measuring instruments, measuring systems and sensors, a so-called confidence level can be determined which, if necessary, can be continually updated during operation whereby additionally a logical relationship to the selected measuring task can be taken into account. Thus, it becomes possible in the interest of quality assurance for certain measuring tasks (e.g. unmanned, automatic testing operation) to define a minimum confidence level for a test stand for example.

In order to guarantee the required flexibility of the plausibility and confidence monitoring for each current configuration of a test run, the confidence level of at least one of the measured values for a changed test system is re-determined and updated, according to another characteristic of the invention, at each change in the type and/or number of plausibility nodes and/or the type and/or number of signal channels.

In the above-mentioned method, the value for the confidence level is advantageously processed together with the measured value in order to take it into account simply and quickly.

According to a special embodiment, a respective value for the confidence level can be determined separately for various partial systems while the modularity of the system is maintained.

If, according to a further characteristic of the invention, one or several partial elements are mathematically selected from a group of signal channels, sensors and/or plausibility nodes, combined with the current configuration of the test system or partial system, and the hypothetical new confidence level is ascertained, then any change in the overall system can be detected early in respect of said confidence level's influence on the plausibility of the test results, the reliability of the measuring results and non-permissible deviations. Thus, the plausibility and quality of the results obtained can be signalled to the user not only after a test run has been carried out, but advantageously already prior to start-up so that, in case of negative effects from the changes carried out or planned, the test run which thus would not provide useful results would not have to be carried out in the first place. For example, by adding a certain signal channel, which increases the redundancy of measured data with a suitable confidence level range, a higher confidence level can be achieved for the overall system. Thus, the system provides the user automatically or in response to his query with a statement in relation to a general or quite specific test run aim with a statement as to which confidence level he can expect with his current configuration and which confidence level he could obtain by adding further components.

Furthermore, with suitable programming, a statement can also be obtained about which options for the improvement of confidence levels are available and possibly even which options should be selected in preference to others if a relevant message is issued in case of a changed, preferably increased confidence level compared to the initial confidence level.

The advantages of the invention described in the previous paragraphs and of its characteristics lie in the comprehensive concept of a plausibility test for all partial systems of a test system and the possible plausibility statements for both the partial systems as well as the overall system. Furthermore, a confidence level is ascertained which represents a new measure for the meaningfulness of plausibility statements and for the suitability of test stand configurations for certain test tasks. At the same time, there is a high degree of flexibility and also retrofitting capabilities for new test tasks, which can be carried out with little operator effort due to a system-supported, partially automatic parametrising based on 'plug & measure', as a result of the integrated and flexibly extendable, large library of test rules for different test stands and tasks. Of course, the method in terms of the invention is implemented in such a way that it can be used on test stands or test instruments with standardised interfaces (ASAM) and not just for certain proprietary equipment.

In the description below, some of the above-mentioned concepts and the actual invention itself are to be explained in more detail.

The plausibility test nodes, being preferably but not necessarily defined generally at the software level in terms of object oriented programming of open system, are "activated" for a certain structure of the system comprising test piece and test system, a test stand for example, by allocating a test rule and an associated structure from the existing albeit extendable or adaptable library. Input quantities are a list of measured quantities or their measured values required for the application of the test rule, a list of the required virtual quantities or their values, and as a priori knowledge a list of the required parameters or their values. The result quantities of a plausibility node, however, are not necessarily defined in their final form. These could be, e.g.: plausibility yes/no, reference to current test run aim, contribution to the reliability, i.e. the confidence level, of the current partial or overall system. Plausibility test nodes in hardware and circuitry are also possible, in the simplest case it may be to check whether a signal channel is connected at all, whether the relevant data connection has been made, whether a certain minimum signal level has been reached, etc.

This can involve a continuing search for suitable test rules whereby the experience and tools of the various fields such as simulation technology, indicating technology, consumption measuring technology, combustion diagnosis, emission measuring technology, test stand applications, etc. are to be utilised. It should be advantageous to implement and check the test rules at a preliminary stage already in the various test stand measuring instruments and measuring systems. Based on the insights gained thus and using the universal framework of the plausibility test system, the test rule library can then be created, being adapted to a multitude of application options. Finally, the newly developed test rules and the totality of the new tool have to be validated again and again, i.e. they must be checked for actual systems and optimised if necessary.

The method in terms of the invention of plausibility check and confidence level determination is preferably implemented in a stand-alone unit which can be integrated into an existing test system via a data network connection for software modules programmed in the object-oriented method. Namely a dedicated PC for example, which is equipped with the framework software for plausibility tests in general and with at least the software library which contains all the test rules required for the actual test stand and test run.

This is described in more detail based on the following actual example taken from engine test bench measuring technology. A sub-system already equipped for the plausibility and confidence level test in terms of the invention, e.g. a fuel weighing unit, queries via a network connection at the time of the system configuration and parametrising whether the master unit is present in the overall system, which would then reply to the query.

If no, the fuel weighing unit can carry out but a test within its unit and display the result. If yes, the plausibility test is activated in relation to the fuel weighing unit: The data connections are established and it is placed into memory that, in future, certain symptomatic data and possibly also parameters can be supplied by this sub-system and be processed in the possibly many associated plausibility test nodes to obtain the desired plausibility statements. Even from this structure-related information, an evaluation of the future plausibility statements can already be calculated, in particular in relation to the plausibility level, namely in relation to the meaningfulness of various plausibility statements emanating from the structure and the associated redundancy.

Then, when an actual test run is started and measured data is produced, the activated test nodes constantly receive the required input data. From this content-based information, the evaluated plausibility statements are continuously generated and offered to the plausibility test system. This way, still during the test run, it can be determined quickly whether or not the validity or usefulness of the test run still obtains. But even after the test run, the information can be viewed as a final result. A plausibility test based on stored test data after the test run is also possible. As required, the display of the result can take place in a centralised or distributed arrangement.

If the fuel weighing unit installed on the test stand is not yet equipped for a plausibility test and therefore has no direct data connection to the master unit, the master can nevertheless carry out, from the measured values of the test stand weighing unit available (at least in part) in the test stand data capture system, a plausibility check adapted to the available data.

This is made possible by the standardised interfaces and name lists for the measured values of a test stand, in particular an engine test bench, which thus represents an open system.

The special design of the data network allows an arrangement for the plausibility test, which is largely independent of specific hardware. Software modules, e.g. modules of associated plausibility test nodes, can be installed on different computers. Even the integration of special computers for the so-called digital signal processing (DSP) is possible, for example involving the efficient application of plausibility test rules for highly dynamic signal curves in real time.

What is claimed is:

1. A method for the analysis and evaluation of measured values of an open test system in which a test piece during a test run is monitored by at least one signal channel which sends a signal to an evaluation unit for further processing whereby at least one plausibility node is coupled with at least one signal channel, comprising the step of ascertaining from the type and number of plausibility nodes as well as their possible, variable interconnection an evaluated plausibility for at least one of the measured values, wherein from the type and number of available plausibility nodes in combination with the type and number of available signal channels, a value can be ascertained for the confidence level of the plausibility of at least one of the measured values of the current test system.

2. The method according to claim 1, wherein at least some of the plausibility nodes are selected from a totality of predefined plausibility nodes stored in a library.

3. The method according to claim 2, wherein the library of plausibility nodes is extendable and changeable.

4. The method according to claim 1, wherein the evaluated plausibility is ascertained separately for various partial systems.

5. The method according to claim 1, wherein for each change of the type and/or number of plausibility nodes and/or the type and/or number of signal channels, the value for the confidence level of at least one of the measured values for the now changed test system is ascertained a new and made current.

6. The method according to claim 5, wherein the value for the confidence level is processed further together with the measured value.

7. The method according to claim 6, wherein one value each is ascertained separately for the confidence level of different partial systems.

8. The method according to claim 7, wherein from a group of measuring channels, sensors and/or plausibility nodes, one or more partial elements are selected analytically, are combined with the current configuration of the test system or partial system and the hypothetical new confidence level is determined.

9. The method according to claim 8, wherein in case of a changed, preferably increased confidence level compared to the initial confidence level, an appropriate message is issued.

* * * * *